United States Patent [19]
Beczak, Sr. et al.

[11] Patent Number: 5,634,891
[45] Date of Patent: Jun. 3, 1997

[54] ORTHOTIC APPARATUS USEFUL FOR TREATING PAIN ASSOCIATED WITH SPINAL DISORDERS

[75] Inventors: Terry A. Beczak, Sr., Wichita, Kans.; Thomas E. Szymke, Savannah, Ga.

[73] Assignee: Peach, U.S., Inc., Wichita, Kans.

[21] Appl. No.: 421,764

[22] Filed: Apr. 14, 1995

[51] Int. Cl.⁶ .................................. A61F 5/00; B24B 7/00
[52] U.S. Cl. ........................... 602/19; 450/119; 450/121
[58] Field of Search ...................... 602/19; 2/311, 2/312; 450/94, 115–117, 119, 121–125

[56] References Cited

U.S. PATENT DOCUMENTS

| Re. 31,564 | 4/1984 | Hendricks . | |
|---|---|---|---|
| 1,256,603 | 2/1918 | Somers | 450/121 X |
| 1,727,668 | 9/1929 | Parkison | 450/124 X |
| 1,790,792 | 2/1931 | Camp | 450/125 X |
| 2,793,368 | 5/1957 | Novel | 450/119 |
| 3,097,640 | 7/1963 | Morgan | 602/19 |
| 3,926,183 | 12/1975 | Spiro | 602/19 |
| 3,927,665 | 12/1975 | Wax | 602/19 |
| 4,173,973 | 11/1979 | Hendricks . | |
| 4,508,110 | 4/1985 | Modgiun | 602/19 |
| 4,821,739 | 4/1989 | Willner et al. . | |
| 4,926,502 | 5/1990 | Miyamura . | |
| 5,135,471 | 8/1992 | Honswerth . | |
| 5,192,305 | 3/1993 | Sastre . | |
| 5,226,874 | 7/1993 | Heinz et al. . | |

Primary Examiner—Linda C. Dvorak
Attorney, Agent, or Firm—Shook, Hardy & Bacon L.L.P.

[57] ABSTRACT

A corset-type orthotic device is provided for treatment of lower back pain by causing uniform abdominal compression. The corset utilizes vertically spaced apart straps which overlap at the front of the corset to cause tightening of the corset about the torso of the wearer to increase the abdominal compression. The straps are connected at one end to lateral margins of a front panel of the corset and extend rearwardly through metal rings fixed to lateral margins of a rear panel of the corset. The straps then extend forwardly for joinder at the front panel. Upper and lower ones of the straps are also coupled and extend through another metal ring which allows the straps to vary in length to accommodate the variations in circumference of the lower ribs, waist and hips.

18 Claims, 3 Drawing Sheets

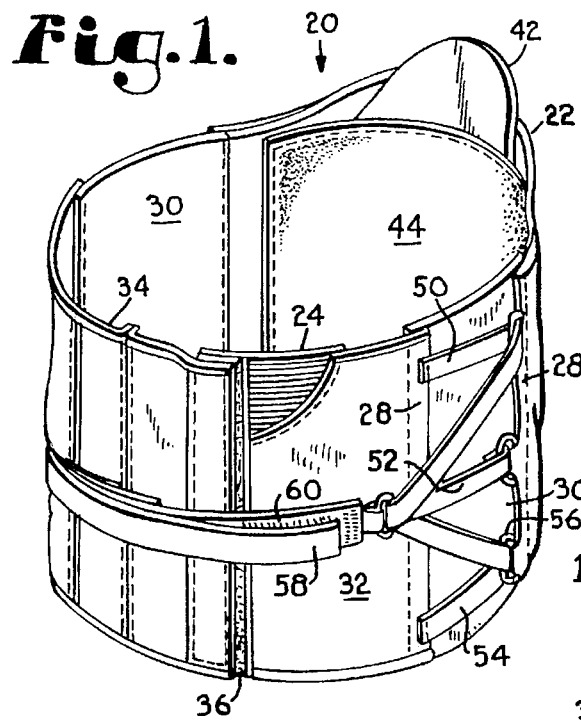
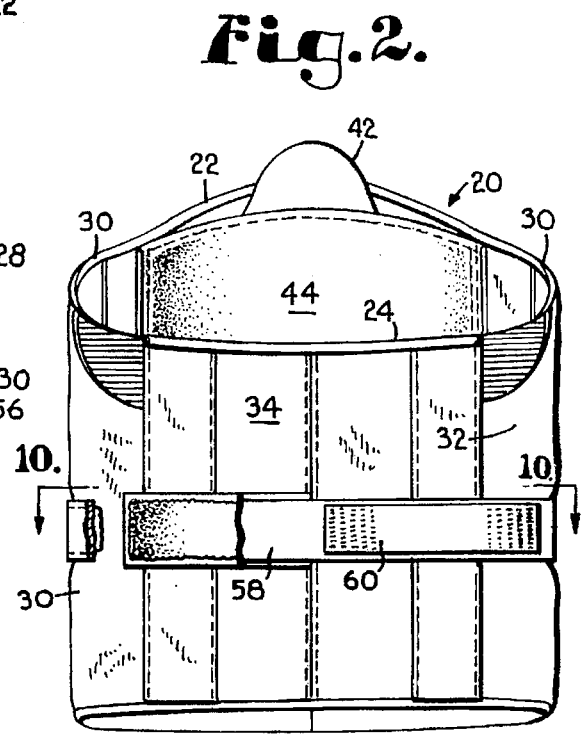
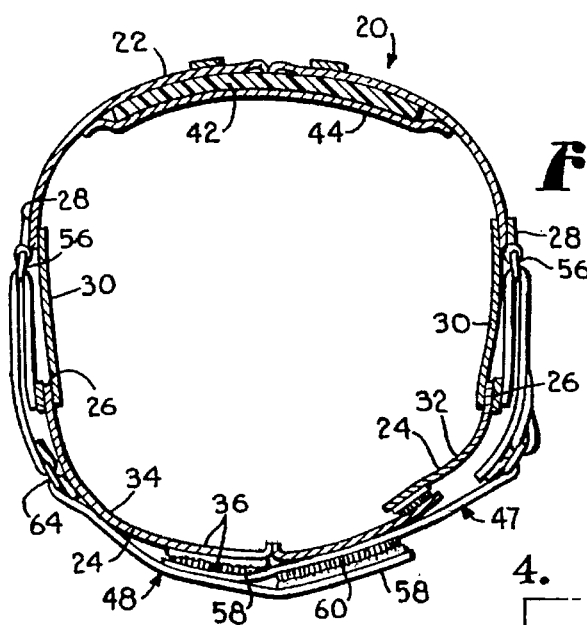
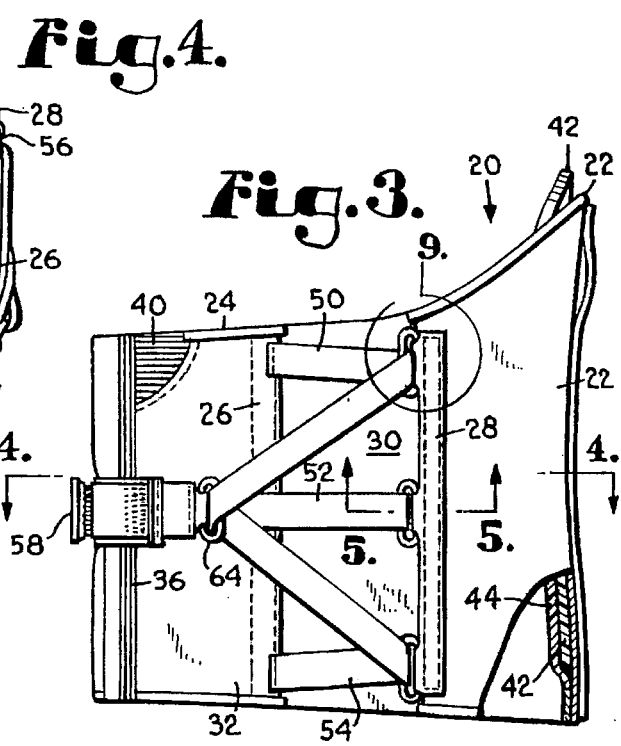
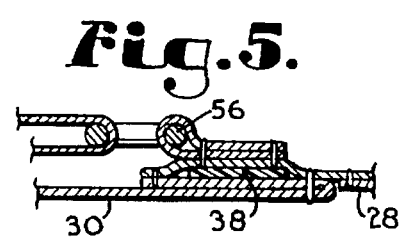

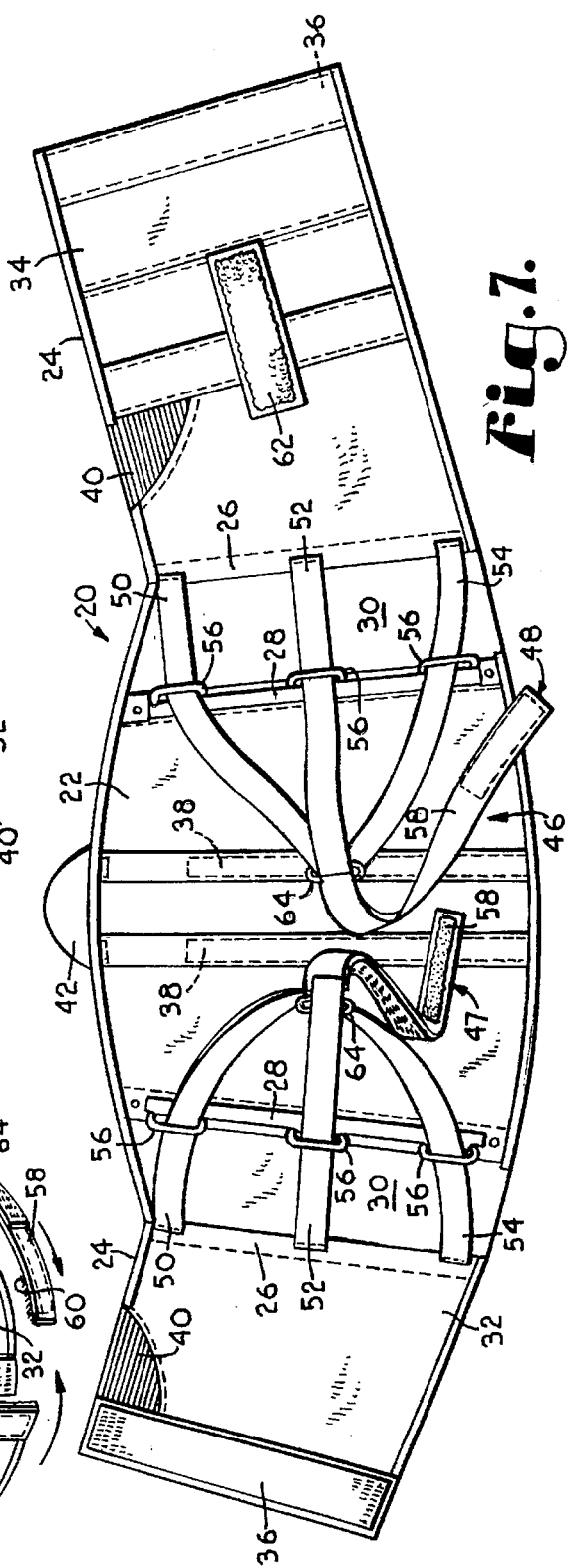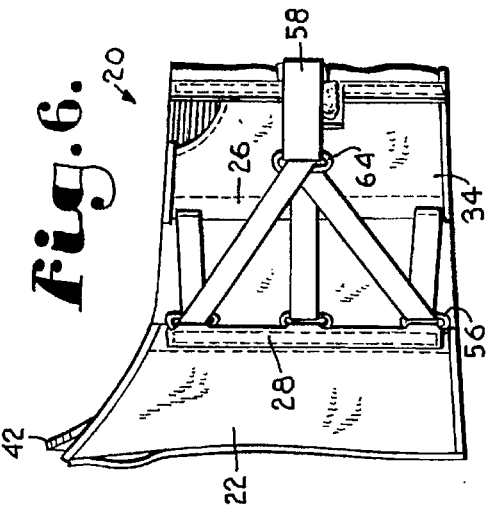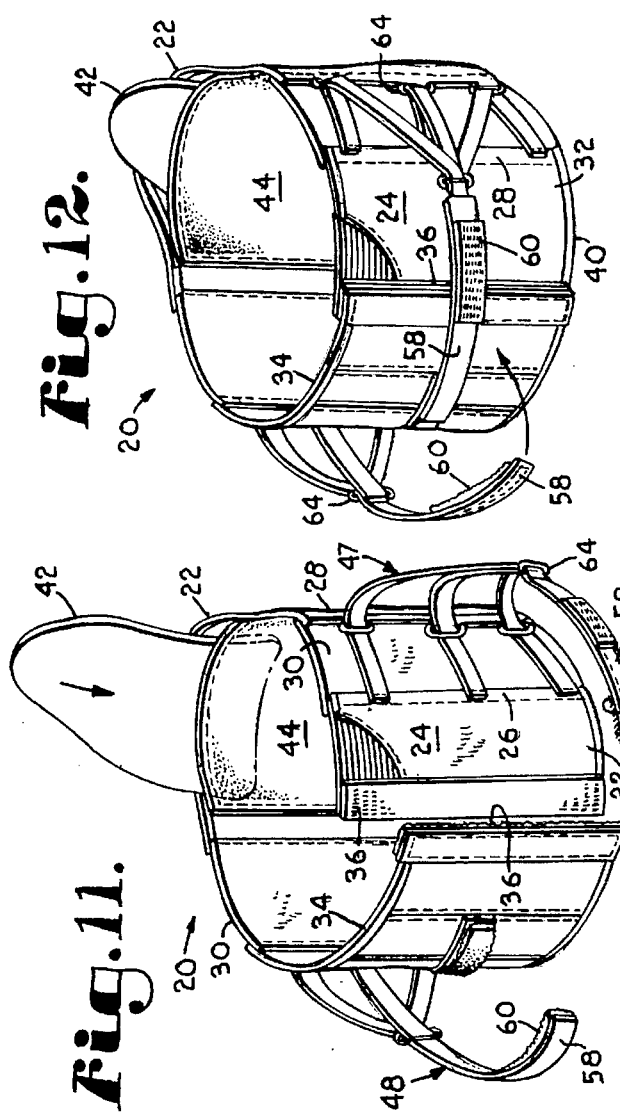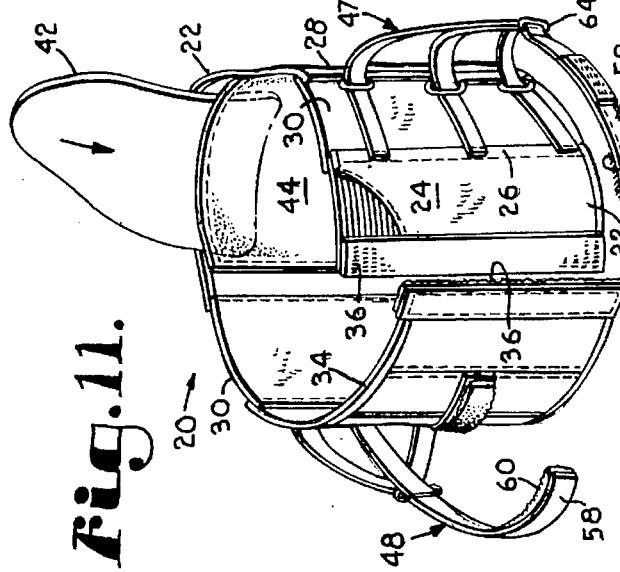

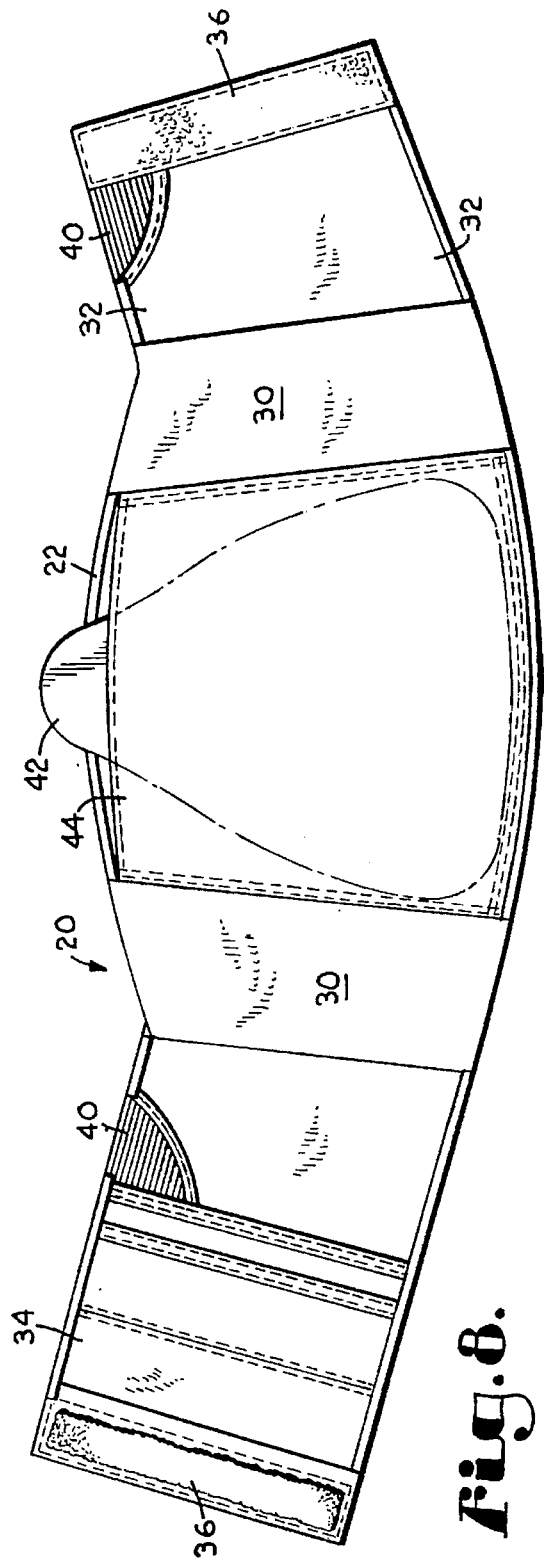
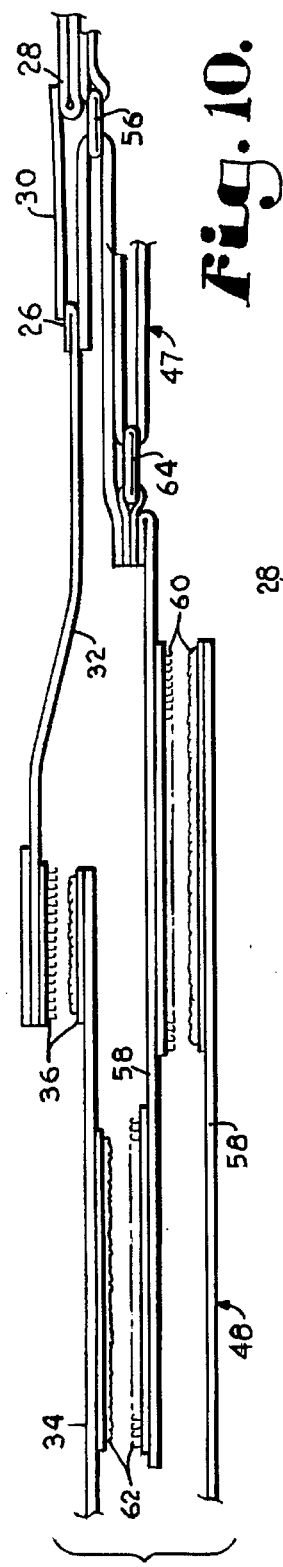
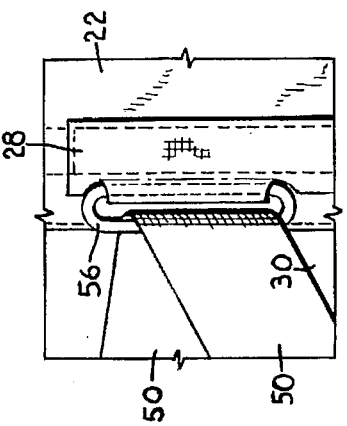

ORTHOTIC APPARATUS USEFUL FOR TREATING PAIN ASSOCIATED WITH SPINAL DISORDERS

BACKGROUND OF THE INVENTION

The invention is directed to braces or orthotic devices used in the treatment of spinal disorders and, more particularly, to an abdominal corset-type orthotic which is used in the treatment of lumbar spine disorders.

It has long been recognized that certain types of lower back pain in humans can be treated by wearing corset type devices. These devices are applied around the torso of the individual and are tightened to cause an increase in the intra-abdominal pressure in the wearer. The increased intra-abdominal pressure in turn functions to reduce the compression force on the individual's spine by creating a semi-rigid hydra-pneumatic cylinder surrounding the spinal column. The load normally carried by the spine is distributed across this cylinder and the pressure on the lumbar inter-vertebral discs is correspondingly reduced. In many cases, the reduction in pressure also serves to provide dramatic relief in the pain associated with the spinal disorder.

One problem associated with many corsets of the type described above is the difficulty in achieving the proper tensioning of the corset about the individual's torso. Typically, the corsets comprise front and back panels which are laced together along their lateral edges by at least one and often several laces. Tensioning of the corset is accomplished by pulling tightly and then securing the laces after the corset has been applied to the torso. It can be appreciated that the use of both hands is generally necessary to pull the ends of the laces to achieve the desired tensioning and then secure them together. The positioning of the laces at the sides of the individual also makes it difficult, particularly for the elderly and infirm, to reach the laces with both hands, let alone manipulate and pull the laces with the force necessary to achieve satisfactory abdominal compression.

Another problem associated with such corsets is the difficulty in achieving uniform tensioning of the corset because of the often wide variations in circumference about an individual's lower ribs, waist and hips. The use of several vertically spaced laces along the lateral edges of the front and back panels of the corset facilitates the adaptation of the corset to the specific contours of the wearer and allows separate tensioning of the upper, lower and intermediate portions of the corset. However, the process of sequentially tightening and readjusting these various laces to achieve the necessary abdominal compression can be very time consuming and difficult, particularly for elderly and infirm patients. Often, one or more previously tied laces must be loosened or further tightened as more laces are tied together or in response to patient discomfort.

In an attempt to overcome the difficulties associated with the use of lateral laces as described above, corsets have been designed which utilize fixed or adjustable hook and loop type fasteners. The hook and loop elements form a vertical seam which can be opened by separation of the hook and loop fastening elements to allow placement of the corset around the torso of the individual. The seam can then be reformed by simply pressing the fastening elements together. While the use of a fastener of this type greatly simplifies the application of the corset to the body, it is still difficult to pull the ends of the corset together with sufficient force to achieve abdominal compression and then join together the elements of the fastener.

A need has thus developed for a corset which can be readily applied, even by elderly and infirm individuals, to achieve a uniform and sufficient amount of abdominal compression to alleviate the pain or discomfort associated with lumbar spinal disorders.

SUMMARY OF THE INVENTION

It is an object of this invention to provide an improved orthotic device which can be applied about the torso even by elderly and infirm individuals to achieve sufficient abdominal compression to alleviate back pain associated with disorders of the lumbar portion of the spinal column.

It is another object of this invention to provide a corset-type orthotic device with tensioning and closure straps that are self-adjusting to achieve uniform tensioning of the upper, lower and intermediate portions of the corset.

It is also an object of this invention to provide a corset as described which can be easily applied and tightened using only one hand so that the corset can be utilized by those individuals who would otherwise have difficulty applying corsets of conventional design.

It is a further object of this invention to provide a corset which utilizes a pulley-type fastening mechanism to provide a leverage advantage which allows the wearer to more easily achieve the desired intra-abdominal compression.

It is a still further object of this invention to provide a corset which utilizes a low-friction fastening mechanism so that the intra-abdominal compressive force can be readily released when removal of the corset is desired.

To achieve these and other related objects of the invention, a corset is provided which is adapted to be wrapped around the torso of a human body to cause an increase in intra-abdominal pressure and a relief in pain associated with disorders of the spinal column. The corset comprises a back panel which is formed to overlie lumbar, pelvic and lower thoracic regions of the spinal column at the center of the back of the human body, a front panel adapted to overlie an abdominal portion of the human body and strap means connecting said back panel with the front panel for allowing the back panel and front panel to be uniformly tightened about the torso to cause the increase in intra-abdominal pressure. The strap means comprises a right strap coupling right lateral portions of said back and front panels and a left strap coupling left lateral portions of said back and front panels, each of said right and left straps further comprising vertically spaced belts secured at one end to the respective lateral portion of the front panel and extending rearwardly through retention members fixed at vertically spaced positions on the respective lateral portion of the back panel and then forwardly for joinder at the front panel. The belts are longitudinally extensible through the retention members to permit adjustment of a distance of separation between the respective right lateral portions of the back and front panels and the left lateral portions of the back and front panels. Notably, the belts are joined together in a manner which allows a leveraged circumferential compressive force to be exerted by the corset on the torso, the compressive force being substantially uniform along the vertical length of the corset.

BRIEF DESCRIPTION OF THE DRAWINGS

In the accompanying drawings which form a part of the specification and are to be read in conjunction therewith and in which like reference numerals are used to indicate like parts in the various views:

FIG. 1 is a perspective view of a corset-type orthotic device of the present invention;

FIG. 2 is a front elevation view of the corset;

FIG. 3 is a side elevation view of the corset and with a portion of the corset broken away to show the positioning of a back board within a pocket in a back panel of the corset;

FIG. 4 is a top plan view of the corset taken in horizontal section along line 4—4 of FIG. 3 in the direction of the arrows;

FIG. 5 is an enlarged fragmentary view of one of the corset straps taken in horizontal section along line 5—5 of FIG. 3 in the direction of the arrows;

FIG. 6 is a side elevation view of the corset illustrating, on a slightly reduced scale, the side opposite from that shown in FIG. 3;

FIG. 7 is an elevation view of the corset which has been laid flat to better show the exterior of the corset;

FIG. 8 is an elevation view similar to that shown in FIG. 7 but showing the inside of the corset;

FIG. 9 is an enlarged side elevation view of an upper ring-type fastening taken from within the circle indicated in FIG. 3;

FIG. 10 is a somewhat schematic exploded view of the front portion of the corset taken in horizontal section along line 10—10 of FIG. 2 in the direction of the arrows;

FIG. 11 is a perspective view of the corset illustrating the insertion of the rigid back board into its receiving pocket and fastening of the left and right corset straps; and FIG. 12 is a perspective view of the corset similar to the view shown in FIG. 11 but showing the fastening of the right corset strap.

DETAILED DESCRIPTION OF THE PREFERRED EMBODIMENTS

Referring now to the drawings in greater detail and initially to FIGS. 1–4 and 6, a corset of the present invention is designated broadly by the numeral 20 and is shown in a configuration resulting from application of the corset 20 to the trunk or torso of a male or female human body. The corset 20 functions to reduce lower back pain in part by stabilizing the spinal column against undesired movement and maintaining the spine in the desired alignment. The corset 20 also serves to reduce lower back pain by increasing the intra-abdominal pressure to create a semi-rigid, hydra-pneumatic cylinder surrounding the spinal column. The cylinder shares the load normally carried by the spinal column and thereby reduces the vertical compression force exerted on the spine and the intervertebral disks which separate the spinal vertebrae.

Corset 20 comprises a back web or panel 22 which is formed to overlie the portion of the spinal column known as the lumbar region at the lower back of the human body. The back panel 22 may, and preferably does, have a vertical length to also overlie the lower thoracic portion of the spinal column at its upper end and the pelvis at its lower end. This vertical extension of the back panel 22 is advantageous because the pelvis and lower ribs serve to brace the lumbar, including against rotation.

The corset 20 also includes a front web or panel 24 which is formed to overlie the abdominal cavity or region at the front of the human body. The front panel 24 is coupled at its left and right lateral margins or edges 26 to corresponding left and right lateral edges 28 of the back panel 22 by side panels 30.

The front panel 24 of corset 20 is separated into left and right panels 32 and 34 which partially overlap and are joined together by a releasable fastener 36 along their vertical lengths to form a releasable seam. The seam allows the corset 20 to be opened as illustrated in FIGS. 7–8 to facilitate application and removal of the corset. The fastener 36 preferably comprises hook and loop type elements sold under the Velcro brand name but other types of fasteners could be used if desired. The fastener 36 should be capable of withstanding large shear stresses but should allow the left and right panels 32 and 34 to be readily joined and separated to allow the corset 20 to be easily applied and removed by the wearer. If desired, the seam formed by fastener 36 could be located elsewhere on the corset, such as in either side panel 30 or, less desirably, in back panel 22.

Various types of materials may be used in the construction of back panel 22, front panel 24 and side panels 30. Preferably, at least portions of the panels are formed of non-stretchable materials to allow a suitable compressive force to be exerted by the panels in the manner described below. Typically, the panels will be formed of textile fabrics such as cotton but synthetic fabrics as well as non-woven materials could be used instead. The panels 22, 24 and 30 can be formed from separate pieces of the same or different materials which are sewn or otherwise joined together along their lateral edges. Alternatively, a single piece of material can be used to form the panels. A plurality of stays 38 can also be formed in the panels to provide vertical support for the panels.

The corset 20 optionally includes elastic sections 40 which are formed of stretchable or elastic material to allow the corset to conform to the physical variations of the individual wearing the corset 20. The elastic sections 40 are preferably positioned only at the upper margin of the corset 20 so that generally continuous center and lower bands of non-stretchable material are presented by the panels 22, 24 and 30. Although the size, shape and placement of the elastic sections 40 can be varied as desired, it is generally preferred that the elastic sections be placed at the upper margin of the front panel 24.

A rigid back board 42 is also included in the corset 20 to provide a broad rigid surface to support and stabilize the spinal column. The back board 42 is removably positioned within a pocket 44 formed on a forward surface of the back panel 22. The back board 42 is preferably formed of a thermoplastic material to permit the back board to be specifically conformed to the contours of the lower back of the individual wearing the corset 20. An example of a suitable material is a low temperature thermoplastic sold by Johnson & Johnson under the trademark Orthoplast. If desired for comfort purposes, a forward face of the back board 42 can be covered with a pad such as formed of a polyethylene foam.

In accordance with the present invention, leveraged circumferential pressure, with resulting increased intra-abdominal pressure, is exerted by the corset 20 on the trunk or torso of the individual wearer through the use of suitable strap means 46 which join together the front and back panels 24 and 22. The strap means 46 comprises a left strap 47 and a right strap 48 which are operable to draw the lateral edges of the back panel 22 toward the lateral edges of the front panel 24. The free ends of the straps 47 and 48 may be fastened at the front of the corset 20 to allow the wearer of the corset to gain a mechanical advantage when tensioning the straps to cause exertion of the circumferential pressure on the wearer's torso. Notably, the straps 47 and 48 utilize a pulley-type system which leverages the applied mechanical force so that increased intra-abdominal compression can be obtained.

Both of the left and right straps 47 and 48 are formed of generally non-stretchable material and comprise vertically spaced apart upper, intermediate or center and lower belts 50, 52 and 54. Each belt 50, 52 and 54 is secured at one end to a respective lateral edge of the front panel 24 with the upper belt 50 being located at the upper vertical margin, the lower belt 54 being located at the lower vertical margin and the center belt 52 being located at a vertically intermediate position on the corset 20. The belts then extend rearwardly from their respective areas of attachment at the lateral edges of the front panel 24 and are coupled with the corresponding lateral edges of the back panel 22 in a pulley-type arrangement. The belts are coupled with the lateral edges of the back panel 22 by individual fastening elements 56 which serve as pulleys to permit longitudinal extension of the belts through the fastening elements. Various types of fastening elements 56 can be utilized for this purpose but elongated metal loops or rings as best shown in FIGS. 5 and 9 are generally preferred because of their strength and rigidity. In addition, the metal rings have a low coefficient of friction which minimizes the wear on the belts 50, 52 and 54 as they are moved back and forth through the rings. The low coefficient of friction also allows the compressive force exerted by the left and right straps 47 and 48 to be readily released without the time-consuming manipulation of laces or other conventional fastening elements.

In use, the belts 50, 52 and 54 are doubled back upon themselves after passing through their respective fastening elements 56 and extend forwardly to the front of the corset 20 and are coupled together at a vertically intermediate position of the corset. A wider tensioning belt 58 is secured to and is in longitudinal alignment with the center belt 52 of each of the left and right straps 46 and 48. It is to be understood that the each tensioning belt 58 may simply be part of or an extension of the associated center belt 52. The tensioning belts 58 are of a sufficient length to at least partially overlap at the front of the corset 20. The tensioning belts 58 include a suitable fastener 60 such as formed by hook and loop elements which allow the tensioning belts to be joined together at the front of the corset. Preferably, one of the tensioning belts 58 can also be joined to the front panel 24 by another fastener 62. Alternatively, the tensioning belts 58 can simply be fastened together without being joined to the front panel 24 or both tensioning belts 58 can be independently secured to the front panel 24 by fasteners.

The positioning of the tensioning belts 58 at the front of the corset 20 is particularly advantageous because they may be readily grasped and manipulated by most individuals using a natural hand and arm motion. Even weak and infirm individuals are generally capable of exerting sufficient force on the tension belts 58 to cause the necessary constriction of the corset 20 about the individual's torso.

The tensioning belts 58 are also secured to the upper and lower belts 50 and 54 in a manner so that a longitudinal force exerted on each tensioning belt is leveraged and is also uniformly conveyed to the upper and lower belts as well as the center belt 52. The connection of the upper and lower belts to the tensioning belt is notable in this regard because it permits automatic adjustments in the lengths of the upper and lower belts, with an increase in the length of one of the belts causing a corresponding decrease in the length of the other belt. This allows the upper and lower belts 50 and 54 to automatically adjust to accommodate the expected variations in the circumferential dimensions about the wearer's lower ribs, waist and hips. The adjustment of the belt length in this manner also allows each of the upper, center and lower belts 50, 52 and 54 to exert a uniform circumferential pressure on the torso of the wearer at vertically spaced apart locations.

The automatic adjustment of the length of the upper and lower belts 50 and 54 is achieved by forming the upper and lower belts from a single length of material or otherwise joining their free ends together to form a single belt which is extensible through a fastening element 64 joined to an end of the associated tensioning belt 58, preferably near the connection of the center belt 52 with the tensioning belt 58. The fastening element 64 is preferably a metal ring of the type previously described which functions as a pulley to permit ready movement of the single belt through the ring. The fastening element 64 thus allows the upper belt 50 and lower belt 54 to increase and decrease in length as is necessary to accommodate the particular physique of the wearer, with an increase or decrease in one belt causing a corresponding decrease or increase in the other belt. This automatic adjustment in the respective lengths of the upper and lower belts allows a circumferential tensioning force which is uniform along the vertical length of the corset 20 to be applied to the torso of the wearer. It can be appreciated that the uniform tensioning force is desirable not only from a comfort standpoint but also to ensure that the compression force on the spine is uniformly reduced.

Notably, the series of pulley-type fastening elements 64 operate to leverage the mechanical force applied to the left and right straps 47 and 48 by the wearer of the corset 20. This ability to leverage the applied mechanical force allows the desired intra-abdominal compression to be achieved by even weak and otherwise infirm individuals. As a result, such individuals are able to be more self-sufficient than would be possible if conventional corsets were utilized.

As can best be seen in FIGS. 10–12, the corset 20 is applied to the torso of the individual experiencing lower back pain by wrapping the corset 20 about the torso and joining the hook and loop elements which form the fastener 36 at the left and right front panels 32 and 34. The individual can then achieve the desired abdominal compression by simply grasping and pulling the tensioning belt 58 of the left strap 47 across the front of his or her body. Exerting this longitudinally directed force on the tensioning belt 58 causes the associated upper, center and lower belts 48, 50 and 52 to pull the lateral edge of the corset front panel 24 toward the lateral edge of the corset back panel 22. At the same time, the respective lengths of the upper and lower belts 48 and 52 automatically adjust as necessary to permit the corset 20 to conform to the underlying portions of the wearer's body. This pulling action of the belts causes a circumferential force to be exerted on the torso with resulting abdominal compression. Once the desired compression is achieved, the left strap 47 can be secured by joining the associated tensioning belt 58 to the front panel 24 by the use of fastener 62.

After or while the left strap 47 is being tensioned and secured, the right strap 48 can be grasped and likewise tensioned, causing further abdominal compression. The right strap 48 is then secured by overlapping its tensioning belt 58 with the tensioning belt associated with the left strap 47 and joining together the hook and loop elements which form fastener 60. It can be readily appreciated that the desired abdominal compression can be easily obtained with the use of the left and right straps 47 and 48 in the manner described. Remarkably, this compressive force is substantially uniform at the top, bottom and intermediate portions of the corset 20. Individuals, including the elderly and infirm, can thus self-apply the corset 20 and obtain relief from lower back pain with an ease, simplicity and degree of comfort unobtainable with conventional corsets as previously described.

During the initial fitting of corset 20, the back board 42 can be removed from the corset pocket 44 and heated sufficiently to allow deformation. The back board 42 is then returned to the pocket 44 and the corset 20 is applied to the torso in the manner previously described. The compressive force exerted by the left and right straps 47 and 48 causes the malleable back board to closely conform to the contours of the individual's lower back. Once the back board 42 has cooled sufficiently to become rigid, the straps 47 and 48 can be released to remove the compressive force. During subsequent applications of the corset 20, the back board 42 is simply retained within the pocket 44 in the back panel 22.

It will be appreciated that various types of therapeutic heating and cooling devices may be used in conjunction with corset 20. For example, a cooling mechanism which utilizes a circulating coolant can be applied posteriorly of the back board 42 to reduce swelling, facilitate pain relief or to serve other purposes by causing cooling of the individual's back. Similarly, a heating pad or gel may be used for therapeutic purposes. Because the back board 42 is made of a low temperature thermoplastic material, the heating pad should normally be used in place of rather than in combination with the back board 42.

From the foregoing, it will be seen that this invention is one well adapted to attain all the ends and objects hereinabove set forth together with other advantages which are inherent to the structure described.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A corset adapted to be wrapped around a torso of a human body to cause an increase in intra-abdominal pressure and a relief in pain associated with disorders of the spinal column, said corset comprising:

a back panel which is formed to overlie a lumbar region of the spinal column at the center of the back of the human body;

a front panel adapted to overlie an abdominal portion of the human body; and strap means connecting said back panel with said front panel for allowing the back panel and front panel to be uniformly tightened about said torso to cause said increase in intra-abdominal pressure, wherein said strap means comprises a right strap coupling right lateral portions of said back and from panels and a left strap coupling left lateral portions of said back and front panels, each of said right and left straps comprising vertically spaced belts secured at one end to the respective lateral portion of the front panel and extending rearwardly through retention members fixed at vertically spaced positions on the respective lateral portion of the back panel and then forwardly for joinder at the front panel, said belts being longitudinally extensible through said retention members to permit adjustment of a distance of separation between the respective right lateral portions of the back and front panels and the left lateral portions of the back and front panels, wherein said belts comprise an upper belt secured at said one end near an upper margin of the front panel, a lower belt secured at said one end near a lower margin of the front panel and an intermediate belt secured at said one end at a vertically intermediate position on the front panel.

2. The corset as set forth in claim 1, wherein said upper and lower belts in at least one of the left and right straps are coupled such that an increase or decrease in length of the upper belt causes a corresponding decrease or increase in the lower belt.

3. The corset as set forth in claim 2, wherein a forward portion of the intermediate belt in said at least one of the left and right straps is coupled with the associated upper and lower belts so that a pulling force exerted along the longitudinal length of the intermediate belt is leveraged and uniformly transferred to said upper and lower belts to cause a circumferential compressive force to be exerted by the corset on the torso which is substantially uniform along the vertical length of the corset.

4. The corset as set forth in claim 3, wherein said upper and lower belts form a single belt which is longitudinally extensible through a retention member associated with the intermediate strap to permit said upper belt to increase or decrease in length and said lower belt to corresponding decrease or increase in length and to permit said uniform circumferential compressive force to be exerted by the corset.

5. The corset as set forth in claim 4, wherein the forward end of at least one of the intermediate belts includes a tensioning belt which overlaps the front panel and includes a fastener for being secured at the front panel.

6. The corset as set forth in claim 4, wherein the forward end of each of the intermediate belts includes a tensioning belt which overlaps the front panel and includes a fastener for being secured at the front panel.

7. The corset as set forth in claim 6, wherein said front panel includes a left panel and a right panel which are joined together along a seam by a releasable fastener.

8. The corset as set forth in claim 7, including a back board associated with said back panel for holding the lumbar region in a predetermined alignment, said back board comprising a heat deformable material to permit said back board to be formed to a configuration to hold the lumbar region in said predetermined alignment.

9. The corset as set forth in claim 8, including a pocket in said back panel for receiving and retaining said back board.

10. A corset adapted to be wrapped around a torso of a human body to cause an increase in intra-abdominal pressure and a relief in pain associated with disorders of the spinal column, said corset comprising:

a back panel which is formed to overlie a lumbar region of the sinal column at the center of the back of the human body;

a front panel adapted to overlie an abdominal portion of the human body; and strap means connecting said back panel with said front panel for allowing the back panel and front panel to be uniformly tightened about said torso to cause said increase in intra-abdominal pressure, said strap means comprising a right strap coupling right lateral portions of said back and front panels and a left strap coupling left lateral portions of said back and front panels, each of said right and left straps comprising vertically spaced upper, lower and intermediate belts secured at one end to the respective lateral portion of the front panel and extending rearwardly through retention members fixed at vertically spaced positions on the respective lateral portion of the back panel and then forwardly for joinder at the front panel, said belts being longitudinally extensible through said retention members to permit adjustment of a distance of separation between the respective right lateral portions of the back and front panels and the left lateral portions of the back and front panels, said upper and lower belts in at least one of the left and right straps are coupled such that an increase or decrease in length of the upper belt causes a corresponding decrease or increase in the lower belt.

11. The corset as set forth in claim 10, wherein said upper belt is secured at said one end near an upper margin of the front panel, the lower belt is secured at said one end near a lower margin of the front panel and the intermediate belt is secured at said one end at a vertically intermediate position on the front panel.

12. The corset as set forth in claim 11, wherein a forward portion of the intermediate belt in said at least one of the left and right straps is coupled with the associated upper and lower belts so that a pulling force exerted along the longitudinal length of the intermediate belt is leveraged and uniformly transferred to said upper and lower belts to cause a circumferential compressive force to be exerted by the corset on the torso which is substantially uniform along the vertical length of the corset.

13. The corset as set forth in claim 12, wherein said upper and lower belts form a single belt which is longitudinally extensible through a retention member associated with the intermediate strap to permit said upper belt to increase or decrease in length and said lower belt to corresponding decrease or increase in length and to permit said uniform circumferential compressive force to be exerted by the corset.

14. The corset as set forth in claim 13, wherein the forward end of at least one of the intermediate belts includes a tensioning belt which overlaps the front panel and includes a fastener for being secured at the front panel.

15. The corset as set forth in claim 13, wherein the forward end of each of the intermediate belts includes a tensioning belt which overlaps the front panel and includes a fastener for being secured at the front panel.

16. The corset as set forth in claim 15, wherein said front panel includes a left panel and a right panel which are joined together along a seam by a releasable fastener.

17. The corset as set forth in claim 16, including a back board associated with said back panel for holding the lumbar region in a predetermined alignment, said back board comprising a heat deformable material to permit said back board to be formed to a configuration to hold the lumbar region in said predetermined alignment.

18. A corset adapted to be wrapped around a torso of a human body to cause an increase in intra-abdominal pressure and a relief in pain associated with disorders of the spinal column, said corset comprising:

a back panel which is formed to overlie a lumbar region of the sinal column at the center of the back of the human body;

a front panel adapted to overlie an abdominal portion of the human body;

side panels joining said back and front panels;

a right strap coupling right lateral portions of said back and front panels and a left strap coupling left lateral portions of said back and front panels, each of said right and left straps comprising vertically spaced upper, lower and intermediate belts secured at one end to the respective lateral portion of the front panel and extending rearwardly through retention members fixed at vertically spaced positions on the respective lateral portion of the back panel and then forwardly for joinder at the front panel, said belts being longitudinally extensible through said retention members to permit adjustment of a distance of separation between the respective right lateral portions of the back and front panels and the left lateral portions of the back and front panels, said upper and lower belts in at least one of the left and right straps being coupled such that an increase or decrease in length of the upper belt causes a corresponding decrease or increase in the lower belt, a forward portion of the intermediate belt in each of the left and right straps being coupled with the associated upper and lower belts so that a pulling force exerted along the longitudinal length of the intermediate belt is leveraged and uniformly transferred to said upper and lower belts to cause a circumferential compressive force to be exerted by the corset on the torso which is substantially uniform along the vertical length of the corset.

* * * * *